United States Patent [19]

Furlong et al.

[11] Patent Number: 5,258,034
[45] Date of Patent: Nov. 2, 1993

[54] FEMORAL PROSTHESIS

[76] Inventors: Ronald J. Furlong, 149 Harley Street, London W1N 2DE, England; Johannes F. Osborn, deceased, late of Bonn, Fed. Rep. of Germany; by Gerda Ossenkopp, executor, Birnbaumskamp 7, 3200 Hildesheim, Fed. Rep. of Germany; by Eva-Maria Berg, executor, Sedan Strasse 47, 3200 Hildesheim, Fed. Rep. of Germany; by Helga Schönekas, executor, Birnbaumskamp 7a, 3200 Hildesheim, Fed. Rep. of Germany

[21] Appl. No.: 796,270

[22] Filed: Oct. 11, 1991

[30] Foreign Application Priority Data

Feb. 15, 1989 [GB] United Kingdom ............... 8903464

[51] Int. Cl.⁵ .............................................. A61F 2/32
[52] U.S. Cl. ........................................ 623/23; 623/18
[58] Field of Search .................... 623/16, 18, 19, 23, 623/66

[56] References Cited

U.S. PATENT DOCUMENTS

| | | | |
|---|---|---|---|
| 4,266,303 | 5/1981 | Park | 623/18 |
| 4,280,233 | 7/1981 | Raab | 623/18 |
| 4,495,664 | 1/1985 | Blanquaert | 623/23 |
| 4,539,981 | 9/1985 | Tunc | 606/77 |
| 4,636,214 | 1/1987 | Homsy | 623/23 |
| 4,713,076 | 12/1987 | Draenert | 623/16 |
| 4,990,161 | 2/1991 | Kampner | 623/16 |
| 5,035,713 | 7/1991 | Friis | 623/16 |
| 5,062,854 | 11/1991 | Noble et al. | 623/23 |
| 5,084,050 | 1/1992 | Draenert | 606/77 |
| 5,176,712 | 1/1993 | Homsy | 623/23 |
| 5,181,928 | 1/1993 | Bolesky et al. | 623/23 |

FOREIGN PATENT DOCUMENTS

| | | | |
|---|---|---|---|
| 0169001 | 1/1986 | European Pat. Off. | 623/16 |
| 1213047 | 9/1986 | Japan | 623/16 |

*Primary Examiner*—David Isabella
*Attorney, Agent, or Firm*—Flynn, Thiel, Boutell & Tanis

[57] ABSTRACT

The present invention provides a prosthesis having a stem and upper body part. The upper body part is coated in a material to promote the ingrowth of bone therein and the lower portion of the stem is coated by a material which will be absorbed during the time taken for the prosthesis to be held in place by ingrowth of bone onto the upper body part.

10 Claims, 1 Drawing Sheet

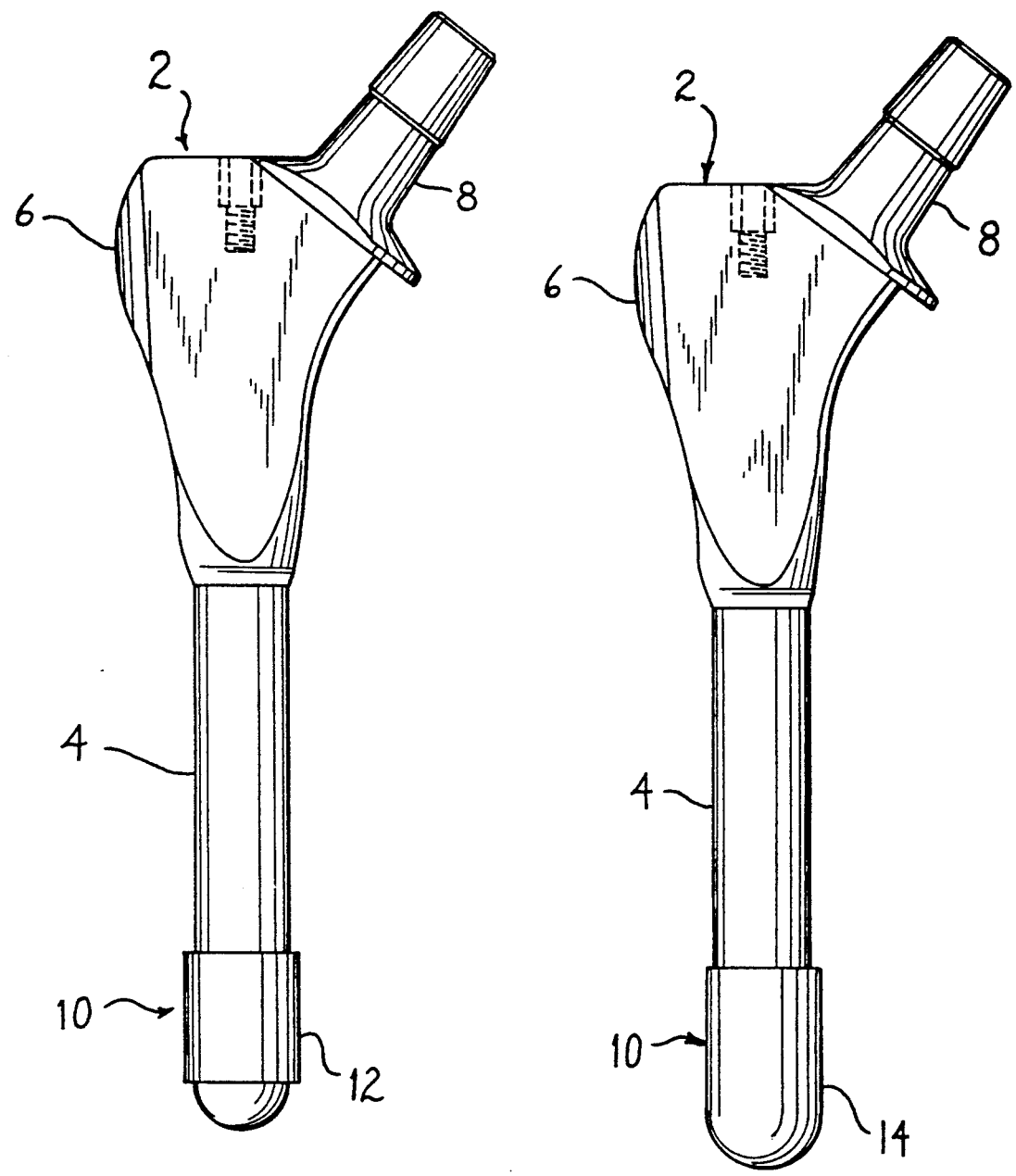

FEMORAL PROSTHESIS

This is a continuation of Ser. No. PCT/GB90/00245, filed Feb. 15, 1990.

This invention relates to orthopaedic prostheses.

"Total-hip replacement" operations are routinely performed with a high success rate. The operation essentially involves replacement of the neck and head of a patient's femur with a femoral prosthesis. The preferred shape of femoral prosthesis has straight stem, an upper body part, and a neck extending from the upper body part and inserted into a ceramic head which is adapted to fit into a cup prosthesis mounted in the patient's acetabular cavity. The stem and upper body part are inserted into the upper end of the tubular shaft of a severed femur which has been suitably prepared. The prosthesis is held in place by the ingrowth of bone onto a coating which has been applied to the stem and upper body part. The coating is of a material that promotes the ingrowth of bone, for example calcium hydroxy-apatite. An example of such a prosthesis is disclosed in UK Patent Application No. 2197204A.

Ingrowth of bone is preferably attained where the coating is in contact with the walls of the tubular shaft. Conventionally the bottom of the prosthesis stem is jammed into the shaft and attachment by the ingrowth of bone will be achieved primarily at the lower stem. This is undesirable. It is preferable to anchor the prosthesis by the ingrowth of bone around the upper body part.

The present invention provides a prosthesis having a stem and upper body part coated in a material to promote the ingrowth of bone, characterized in that the lower portion of the stem is coated by a material which will be absorbed during the time taken for the prosthesis to be accepted by the body. The absorbable material is preferably in the form of a sleeve surrounding the lower portion of the stem. Alternatively the material may be in the form of a sheath covering the distal end of the stem of the prosthesis.

The sleeve or sheath may be preformed from a sheet of absorbable material to be fitted around the stem of the prosthesis as desired.

The thickness of the coating will be such as to give a tight fit of the lower portion of the stem of the prosthesis in a tubular cavity which has been suitably prepared by drilling to a diameter one to a few millimetres larger than the stem of a conventional prosthesis. A uniform coating of constant thickness will ensure the central positioning of the stem in the drilled shaft.

The present invention further provides a method for retaining a femoral prosthesis having a stem and upper body portion in a desired orientation when the stem and upper body portion is inside a tubular cavity which has been suitably prepared which method comprises coating the lower portion of the stem with a material that is absorbed by the body during the time taken for the ingrowth of bone onto the upper portion of the stem and onto the upper body portion to anchor the prosthesis in the said desired orientation.

In the context of this application the time taken for the prosthesis to be accepted by the body refers to the time taken for the ingrowth of bone onto the prostesis stem and upper body part to anchor the prosthesis in position. This period is typically up to three months after implantation.

In the context of this application, "absorbable" is used to define a material which will be completely assimilated by the body within a certain period, during which period the prosthesis is accepted by the body. During this time the upper body part of the prosthesis will have been fixed in position by bone ingrowth, and the stem will be rigidly held in place, centrally positioned in the cavity. This period will vary with the variation of the rate of bone growth from patient to patient. The rate of absorption of the material may be altered by changing the absorbable material, but a material which will be absorbed within a period of 3 months after implantation is most preferred. Once the material has been absorbed, further ingrowth of bone will secure the lower stem of the prosthesis.

The invention will be explained in more detail in the following on the basis of the figures in which:

FIG. 1 is a side view of a femoral prosthesis of one embodiment of the invention, FIG. 2 is a side view of a femoral prosthesis of another embodiment of the invention.

The material chosen should satisfy several criteria. It should be non-toxic; biocompatible; non-reactive with the coating which promotes bone growth; and able to withstand conventional sterilization techniques. The products on absorption must likewise be biocompatible, non-toxic and non-reactive.

The preferred material is a homopolymer or copolymer of lactide and glycolide, some of which are described in U.S. Pat. Nos. 3,636,956 and 3,565,869. The most preferred material is a (D.L.-lactide-co-glycolide) copolymer with an 85:15 ratio of lactide to glycolide such as that obtainable from Boehringer Ingelheim under the trade name RESOMER RG858. The polymer preferably has an inherent viscosity of around 1.4. The ratio of lactide to glycolide in the copolymer can be altered to give copolymers with differing rates of absorption in the body.

Other materials which would likewise be described as absorbable and could be used in the present invention are, for example disclosed in UK Patent No. 1,583,390, poly (p-dioxanone), poly (alkylene oxalate), copolymers of vinyl acetates with unsaturated carboxylic acids (e.g. crotonic, acrylic and methacrylic acids); water soluble or dispersible cellulose derivatives (e.g. methyl cellulose, hydroxymethylcellulose and carboxymethyl cellulose); natural gums; ethylene oxide polymers; polyacrylamide; collagen; gelatin; poly-amino acids; polyvinyl alcohol; polyvinyl pyrrolidone; and triglycerides which are precursors of polymers formed in situ by cross-linking.

Femoral prostheses are available in a variety of sizes to accommodate the different sizes of tubular cavities in patients. It is preferred that about a third to a sixth of the length of the stem is coated by the absorbable material. For example the distal end of the prosthesis may be coated to a length of 2-3 cm at a thickness of 1-2 mm.

The coating may be applied by a melt procedure. The absorbable material melts at a temperature which will not affect the coating which promotes the ingrowth of bone and so the prosthesis stem may be dipped to a desired length in molten material. Removal into a cooler environment will lead to solidification of the material, which will thus adhere to the stem. The rate of cooling may be selected to give a desired thickness of coating. Provided the stem is held exactly vertically on cooling, a symmetrical coating will be obtained. This process produces a sheath around the lower portion of the stem, the distal end of the stem being covered by material.

Alternatively the coating may be applied to form a sleeve around the stem of the prosthesis, leaving the distal end of the stem uncoated. The sleeve should stay in position on the lower portion of the stem as the prosthesis is introduced into the tubular cavity due to there being sufficient friction between the sleeve and the coating to promote bone growth, this coating being of a granular nature.

In accordance with FIG. 1 or FIG. 2, either the sleeve 12 or the sheath 14 may be preformed from sheet material which has been wrapped around a former and heat treated to form the required seals.

A preferred embodiment of the invention comprises a straight stem prosthesis 2, the stem 4 of which has a length of circular cross section, 1 having an upper body part 6 and a neck 8 extending from the upper body part which receives a ceramic head, which head is in turn adapted to be received in a prosthetic cup which is fitted into a prepared acetabular cavity.

The prosthesis is formed as a single finished forging from titanium, steel ar a titanium/vanadium/aluminium alloy. The stem and upper body part are coated with calcium hydroxy-apatite. The lower portion 10 of the stem is coated to a length of 2-3 cm from the distal end of the stem with a sleeve 12 of absorbable material which has been preformed from a sheet of material 1-2 mm thick. The absorbable material is poly(D.L. lactide-co-glycolide) with a lactide to glycolide ratio of 85:15.

In use the severed femur of the patient is prepared as for the insertion of a conventional prosthesis except that the tubular cavity is drilled to a diameter 1-2 mm larger. The prosthesis is inserted into the prepared cavity, the thickness of the coating being such as to give a tight fit therein. Ingrowth of bone over a period of 3 months after implantation will not occur around the lower portion of the stem, but ingrowth around the upper body part and the upper portion of the stem will secure the position of the prosthesis. 3 months after implanation the absorbable coating will have been absorbed by the body and bone ingrowth around the lower portion of the prosthesis will then occur.

I claim:

1. A femoral prosthesis having an upper body part and a stem, the upper body part and the stem having a first bone ingrowth promoting coating which is formed from a material which will promote ingrowth of bone onto said upper body part and said stem, said stem having an upper stem portion adjacent to said upper body part and a lower stem portion, only said lower stem portion having a second coating which is formed from a bioabsorbable material which will be absorbed during the time taken for the prosthesis to be held in place by ingrowth of bone onto said upper stem portion and said upper body part wherein said second coating delays the ingrowth of bone around the lower stem portion until the second coating is substantially absorbed.

2. A femoral prosthesis according to claim 1, wherein the second coating formed from a bioabsorbable material has an absorption rate of up to three months after implantation.

3. A femoral prosthesis according to claim 1, wherein the second coating is a homopolymer or copolymer of lactide and glycolide.

4. A femoral prosthesis according to claim 3, wherein the second coating is an 85:15 copolymer of lactide and glycolide: poly(DL lactide-co-glycolide) 85:15.

5. A femoral prosthesis according to claim 1, wherein the second coating is in the form of a sleeve around the lower stem portion.

6. A femoral prosthesis according to claim 1, wherein the second coating is in the form of a sheath covering the lower stem portion.

7. A femoral prosthesis according to claim 5, wherein the sleeve is preformed from a sheet of said material which forms said second coating.

8. A femoral prosthesis according to claim 6, wherein the sheath is preformed from a sheet of said material which forms said second coating.

9. A method of anchoring a femoral prosthesis having a stem and an upper body part in a desired orientation with the stem and the upper body part inside a suitably prepared tubular cavity, said stem having an upper stem portion adjacent said upper body part and a lower stem portion, and said stem and said upper body part having a first bone ingrowth promoting coating of a material which promotes the ingrowth of bone, said method comprising: providing only the lower stem portion with a second coating formed from a material which is absorbed thereby delaying the ingrowth of bone around the lower stem portion during a period of time taken for ingrowth of bone onto the upper stem portion and onto the upper body part to anchor the prosthesis.

10. A method according to claim 9 wherein the second coating is in the form of a sleeve around the lower stem portion.

* * * * *